(12) United States Patent
Stynes

(10) Patent No.: US 10,918,847 B2
(45) Date of Patent: Feb. 16, 2021

(54) IMPLANTABLE INTERFACE DEVICE

(71) Applicant: OzLobsters Pty Ltd, Geelong (AU)

(72) Inventor: Gil Stynes, Geelong (AU)

(73) Assignee: Gil Stynes, Geelong (AU)

( * ) Notice: Subject to any disclaimer, the term of this patent is extended or adjusted under 35 U.S.C. 154(b) by 834 days.

(21) Appl. No.: 15/068,228

(22) Filed: Mar. 11, 2016

(65) Prior Publication Data

US 2016/0263366 A1  Sep. 15, 2016

(30) Foreign Application Priority Data

Mar. 11, 2015 (AU) .................................. 2015900867

(51) Int. Cl.
*A61M 39/02* (2006.01)
*A61F 2/78* (2006.01)
*A61M 25/04* (2006.01)

(52) U.S. Cl.
CPC .......... *A61M 39/0247* (2013.01); *A61F 2/78* (2013.01); *A61M 25/04* (2013.01); *A61M 2039/0261* (2013.01); *A61M 2039/0273* (2013.01); *A61M 2039/0276* (2013.01); *A61M 2039/0279* (2013.01); *A61M 2039/0288* (2013.01); *A61M 2039/0291* (2013.01); *A61M 2205/0272* (2013.01)

(58) Field of Classification Search
CPC .............. A61M 39/0247; A61M 25/04; A61M 2039/0261; A61M 2039/0273; A61F 2/78
USPC ........................................................ 604/175
See application file for complete search history.

(56) References Cited

U.S. PATENT DOCUMENTS

| 4,897,081 A * | 1/1990 | Poirier ................. A61L 29/041 128/DIG. 26 |
| 2012/0310181 A1 | 12/2012 | Kantrowitz et al. |
| 2014/0276454 A1* | 9/2014 | Kuiken ............. A61M 39/0247 604/246 |

FOREIGN PATENT DOCUMENTS

| DE | 202009018617 U1 | 6/2012 |
| EP | 0164896 B1 | 2/1989 |
| EP | 0367354 A1 | 5/1990 |
| EP | 0367354 B1 | 6/1993 |
| EP | 1825839 A1 | 8/2007 |
| GB | 2056282 A | 3/1981 |
| WO | WO-2008062173 A1 | 5/2008 |
| WO | WO-2010096589 A1 | 8/2010 |

(Continued)

OTHER PUBLICATIONS

Australian Patent Application No. 2015900867 Australian Patent Office International-Type Search Report dated Aug. 7, 2015.

(Continued)

*Primary Examiner* — Phillip A Gray
(74) *Attorney, Agent, or Firm* — Wilson Sonsini Goodrich & Rosati

(57) ABSTRACT

An interface device for implantation in a subject includes a tissue integration layer and a crowning element. The tissue integration layer has a porous structure adapted for ingress of tissue to anchor the device when implanted. The crowning element is adapted for epidermal attachment when the device is implanted and is configured such that once implanted, part of the crowning element extends through the epidermis and is accessible from outside the subject's body. The porous structure of the tissue integration layer is interconnected for tissue ingress during implantation.

14 Claims, 8 Drawing Sheets

(56) References Cited

FOREIGN PATENT DOCUMENTS

WO    WO-2012007755 A2    1/2012

OTHER PUBLICATIONS

Stynes et al., Tissue compatibility of biomaterials: Benefits and problems of skin biointegration. ANZ. J. Surg., 78:654-658 (2008).
European Patent Application No. 16159652.3 Extended European Search Report dated Jul. 5, 2016.

* cited by examiner

IMPLANTABLE INTERFACE DEVICE

CROSS-REFERENCE TO RELATED APPLICATIONS

This application claims the benefit of priority from Australian Patent Application No. 2015900867 filed on Mar. 11, 2015, the contents of which are to be taken as incorporated herein by this reference.

FIELD OF THE INVENTION

The present invention relates to implantable devices. It relates particularly but not exclusively to devices that are suitable for medium to long-term implantation within skin or that breach skin to sit within deeper tissues. Such devices may be used for vascular access, access to body cavities, coupling of prosthetics, reconstruction of tissue and the like.

BACKGROUND TO THE INVENTION

Medical implants include devices that are placed within tissue or breach skin to treat, stabilise, remediate, or obviate a range of medical conditions. The development of biocompatible materials has facilitated the design and manufacture of a vast number of devices that are used in the body or that breach skin, but failure at the interface between the device material and the skin and infection of implants are problems that have proven to be unsolvable.

Implantable devices that breach skin eventually fail and become infected due to failure of skin to attach to the devices. This failure of attachment is consequential to three interrelated pathophysiological phenomena: epidermal marsupialisation, whereby epidermis grows under and around the implant, rather than attaching to it; avulsion, whereby skin pulls away from implant; and infection which complicates and exacerbates the other two phenomena. Achieving a marsupialisation-free, avulsion-free, and infection-free interface and method for implantation has the potential to revolutionise medical practice, permitting long-term and infection-free access to vascular and body cavities, and fully implantable robotics, prosthetics, and other such devices.

Porosity in skin-implanted devices has been shown to increase implantation longevity. However, a permanent, robust and infection-free design and method for implantation has proven elusive. A device and method for implantation that enables skin attachment would be a quantum improvement upon what is currently available.

The discussion of the background to the invention included herein including reference to documents, acts, materials, devices, articles and the like is included to explain the context of the present invention. This is not to be taken as an admission or a suggestion that any of the material referred to was published, known or part of the common general knowledge in Australia or in any other country as at the priority date of any of the claims.

BRIEF SUMMARY OF THE INVENTION

Viewed from one aspect, the present invention provides an interface device for implantation in a subject, the device including: a tissue integration layer having a porous structure adapted for ingress of tissue to anchor the device when implanted; and a crowning element adapted for epidermal attachment when the device is implanted and configured such that once implanted, part of the crowning element extends through the epidermis and is accessible from outside the subject's body; wherein the porous structure of the tissue integration layer is interconnected for tissue ingress during implantation.

Tissue integration into the porous structure of the tissue integration layer may be enhanced by application of a negative pressure to the device during implantation. In a preferred embodiment, the porous structure is macroporous and highly interconnected such that it contains very few or is entirely absent of dead spaces (i.e. non-connected pores). It is also preferred that the tissue integration layer has a compressive strength sufficient to resist complete compression during application of a negative pressure so as to maintain porosity and capacity to allow tissue ingress during the implantation phase.

The interface device is formed from one or more biocompatible materials. Such materials may be selected from the group including but not limited to: a polymer, a metal, a non-metal, a polymer-metal composite, a ceramic and combinations including two or more of the foregoing. In some embodiments, the tissue integration layer and the functional element are formed as a unitary piece although it is to be understood that these parts may be manufactured separately and joined by adhesive, welding, brazing, anchoring or the like.

In some embodiments, one or more of the tissue integration layer, the crowning element and the device as a whole are at least partially flexible. Flexibility permits dynamic integration and movement of the device with surrounding tissue during and after implantation.

Preferably, the tissue integration layer contains highly interconnected pores having diameter of 20 µm to 500 µm to minimise fibroblast death within the pores and collection of cell debris polluting the tissue integration layer. Dead spaces and cell debris can lead to infection, as well as limit ongoing tissue integration into the porous structure. In preferred embodiments, the pores have a diameter of at least 40 µm.

The crowning element is ideally sized and shaped to optimise epidermal attachment, although the shape may be modified according to the application for which the interface device is intended. The shape may be selected from a group including but not limited to toroid, discoid, polygonal, irregular or regular closed shape to name a few.

In some embodiments, the crowning element includes a functionalised zone. Functionalisation may be aimed at increasing epidermal attachment and resisting marsupialisation or in the inverse, resisting epidermal attachment to cause directed marsupialisation. The functionalised zone may be protein optimised e.g. with collagen type 1 or, more desirably, collagen type 4 for enhanced epidermal attachment. The crowning element may also include one or more functionalised zones that are optimised for epidermal attachment or epidermal marsupialisation. The functionalised zones may be provided on the crowning element and may include a junction between the crowning element and the tissue integration layer.

Typically the crowning element is substantially solid and has one or more channels in functional communication with pores of the tissue integration layer. The channels permit the transfer of negative pressure applied during implantation of the device between the crowning element and the pores of the tissue integration layer. Alternatively/additionally, the crowning element includes fenestrations to enhance transmission of negative pressure between the crowning element and the pores of the tissue integration layer. In some embodiments, the crowning element may be completely solid, with negative pressure being applied around it, to the underlying macroporous scaffold into which tissue integrates during implantation.

In some embodiments, at least part of the device is biodegradable in the subject's body. That is, while the product has a stable shelf life, once implanted biological processes within the body cause the biodegradable part of the device to break down and become excreted from the body.

In some embodiments, the crowning element is adapted to be coupled with or receive an accessory device. Once the pores of the tissue integration layer are fully or at least substantially filled with tissue, the implant is securely anchored in vivo and the crowning element can be used to interface with other devices.

In some embodiments, the interface device is required for vascular, tissue, or body cavity access. In such applications, part of the tissue integration layer is removable to extend a channel in the crowning element through the scaffold, thereby providing a continuous channel to access deeper tissues after implantation. Thus, a through channel in the device can provide access to a target vessel, tissues, or cavities. In some embodiments, the through channel provides a portal for removal of fluid from the subject and/or an access point for insertion of an instrument or other accessory device.

In some embodiments, the crowning element is configured to couple with or receive an accessory device such as a trocar, tube, drain, prosthetic, electronic device, robotic device, catheter, ostomy device, drug delivery device, a fixation device, or tissue building scaffold, to name a few. In some embodiments, the crowning element may include magnetic or electronic material to aid coupling with an accessory device.

In some embodiments, the device includes a plurality of crowning elements configured to extend through the epidermis when implanted providing a plurality of access points that are accessible outside the subject's body, with a single tissue integration layer providing an anchor when implanted.

Viewed from another aspect, the present invention provides a method for implanting an interface device for transcutaneous access in a subject, the method comprising the steps of: preparing tissue at an implant site of the subject; placing the interface device, having a porous (preferably macroporous) tissue integration layer and a crowning element at the prepared implant site, with the porous tissue integration layer in contact with the prepared tissue; and applying negative pressure to the device to enhance tissue integration into the pores of the tissue integration layer.

Preferably, preparing the tissue site includes de-epithelializing an area of skin at the implant site; and excising or incising a section of dermis sufficient to accommodate the tissue integration layer. Such steps are ideally performed using known techniques that maintain a sterile environment for implantation of the interface device.

Preferably, the implantation method further includes applying a dressing over the device and the implant site so as to substantially seal off the device and implant site wherein negative pressure is applied through the dressing. In effect, the negative pressure suitable dressing provides hermetic coverage.

The negative pressure can be applied at between negative 25 mmHg and negative 500 mmHg, but is ideally applied at approximately negative 125 mmHg, and is applied for between 1 and 28 days.

In some embodiments, the negative pressure is applied continuously over the implantation period. However, it is to be understood that the negative pressure may be applied for much shorter periods (hours to days), periodically, in bursts or at quasi-random intervals over the course of 1 to 28 days to enhance tissue ingress into the pores of the tissue integration layer. In some embodiments, cycling the pressure between "on" and "off" or "on" and a reduced pressure condition may be preferred.

In some embodiments where a through channel across the device is required for access to deeper tissues, the method includes removing part of the tissue integration layer to provide a through channel across the device for accessing deeper tissues. The removed part of the tissue integration layer may be with or without ingressed tissue. Removal may be by e.g. boring, reaming, drilling, surgical excision, use of a cutting trocar, or twisting of a trocar built into the through channel. Alternatively, a sharp-tipped instrument or object could be pushed through the tissue integration layer to form a through channel without the need to remove a core of the tissue integration layer first.

In some embodiments, the method includes coupling an accessory device to the crowning element, or inserting an accessory device into the crowning element. This can occur at any stage during implantation or after implantation. In some embodiments, use of the implanted device may involve periodically coupling and decoupling an accessory device, such as a peritoneal dialysis catheter. In other embodiments, an accessory device may be permanently coupled. In other embodiments still, no accessory device may be coupled to the interface device.

In some embodiments, the device may be implanted into a first tissue site and then grafted to a different tissue site which may be in the same subject (donor subject), or in a different subject (donee subject). Thus, the method may further include the steps of: after tissue has integrated into the porous structure, excising the implanted device from the implant site; preparing tissue at a recipient site; and placing the excised implanted device at the prepared recipient site.

Viewed from yet another aspect of the present invention, there is provided an implant device for implantation in a human or animal subject, the implant device including: a tissue integration layer having a porous structure for ingress of stabilising tissue to anchor the device when implanted; and a crowning element adapted for epidermal attachment when the device is implanted; wherein the porous structure of the tissue integration layer is configured to enhance tissue ingress during implantation of the device.

The crowning element may include a functionalised zone that is optimised for epidermal attachment.

Preferably, the porous structure of the tissue integration layer is macroporous and with highly interconnected pores to enhance tissue ingress during implantation particularly when negative pressure is applied. The stabilising tissue may include one or more of dermal and subcutaneous tissue and optionally, the tissue integration layer may have a surface with one or more functionalized zones that are optimised for epidermal attachment. Optimisation may be with protein e.g. collagen, particularly collagen type 4. Alternatively/additionally, the crowning element may have one or more functionalized zones that are optimised for epidermal attachment.

It is to be understood that the device may be configured for implantation or grafting wholly or partly internally of the subject's body, or transdermally. The device may be implanted in any type of stabilising tissue such as dermal tissue, subcutaneous tissue, bone, fat, breast, cartilage, organs, fascia, muscle and blood vessel walls. In embodiments where the stabilising tissue is beneath skin, the device may be implanted using an open surgical technique or, in some embodiments, using a minimally invasive or natural orifice insertion technique. Ideally, the porous structure of the tissue integration layer is configured to enhance tissue ingress during implantation, preferably during application of negative pressure. Other features of the implant device may be incorporated, including those that are described in relation to the aforementioned interface device.

Viewed from yet another aspect, the present invention provides a kit including: a piece of macroporous tissue integrating material; and one or more crowning elements attachable to the tissue integrating material; wherein the one or more crowning elements are affixable to the macroporous tissue integrating material to form an implantable interface device for use in a human or animal subject.

The one or more crowning elements may be adapted for epidermal attachment when the device is implanted, and may include one or more functionalised zones that are optimised for epidermal attachment or epidermal marsupialisation.

In some embodiments, the kit includes one or more of an adhesive, a bonding agent and one or more anchors for affixing one or more crowning elements to the tissue integrating material. The kit may also include one or more dressings and tubing for connecting the interface device with a source of negative pressure during implantation.

BRIEF DESCRIPTION OF THE DRAWINGS

The present invention will now be described in greater detail with reference to the accompanying drawings. It is to be understood that the embodiments shown are examples only and are not to be taken as limiting the scope of the invention as defined in the claims appended hereto.

DETAILED DESCRIPTION OF THE INVENTION

Figure 1A:
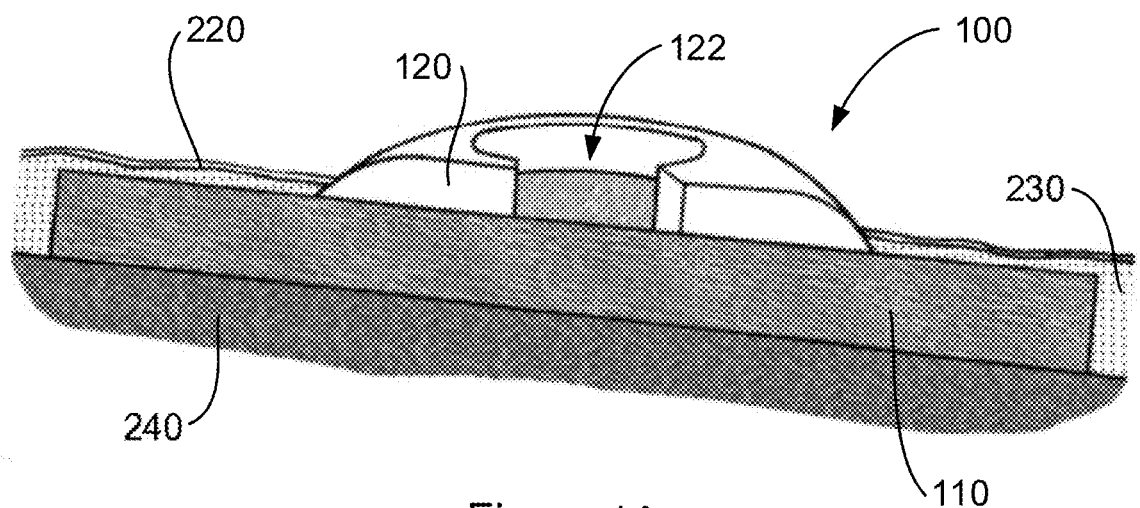
FIG. 1A is a schematic illustration of an interface device according to an embodiment of the invention, shown in cross section.

Various embodiments and features of the invention are discussed herein by reference to the drawings which are not to scale and are intended merely to assist with explanation of the invention. Referring firstly to FIG. 1A, there is shown an interface device 100 for implantation in a subject. In particular, the implant device 100 is shown implanted in a subject's skin, specifically the epidermis 220, dermis 230, and subcutaneous tissue 240.

The device includes a tissue integration layer 110 that has a macroporous structure adapted for ingress of dermal tissue 230 and subcutaneous tissue 240 to anchor the device in place when implanted. The interface device 100 also includes a crowning element 120 which is adapted for location, in the example shown, in at least the epidermis 220 although the thickness of the crowning element may also necessitate placement at least in part in the dermis 230 as shown. Placement of at least part of the crowning element 120 in the epidermis 220 enables epidermal attachment to the crowning element such that part of the crowning element extends through the epidermis when implanted so that it is accessible from outside the subject's body. The porous structure of the tissue integration layer 110 is interconnected for tissue ingress during implantation. This may be enhanced by application of negative pressure to the device during implantation.

Ideally, the tissue integration layer 110 is 25-90% of the thickness of the dermis 230 and is arranged on subcutaneous tissue 240 for implantation. In some embodiments, it is preferable for the tissue integration layer 110 to be thicker or thinner, as may be necessitated by the clinical application for which it is used. Moreover, the tissue integration layer 110 may be placed at a variety of depths within the skin and in some embodiments, may span a number of tissue layers including tissue layers deeper than the skin and subcutaneous tissue 240. Various arrangements of the tissue integration layer relative to the crowning element 120, and various implantation locations in the skin are contemplated within the ambit of the present invention and, ideally with application of negative-pressure, achieve tissue integration into the porous material of the tissue integration layer 110 with epidermal attachment, to the crowning element 120 and/or aspects of the tissue integration layer surrounding the crowning element.

The tissue integration layer 110 has a highly interconnected macroporous structure such that the number of dead spaces (i.e. non-connected pores) are minimised or, in a preferred embodiment, entirely absent. The macroporous structure of tissue integration layer 110 provides a scaffold into which dermal and subcutaneous tissue may integrate, particularly during application during of negative pressure across the interface device 100 during the implantation stage. In a preferred embodiment, the tissue integration layer 110 has such high interconnectivity between pores that it imitates the structure of cancellous (i.e. trabeculated) bone. Such a structure has high interconnectivity as discussed above, as well as structural strength which can withstand the compressive forces applied to the tissue integration layer 110 during application of a negative pressure. In some embodiments, the tissue integration layer 110 may be optimised with antibacterial, cell growth stimulating and other agents that enhance tissue ingress and anchoring of the device in vivo. Once implanted, the tissue integration layer 110 provides a foundation for the crowning element 120 and any accessory devices that may pass through or be attached to it.

In some embodiments, it may be desirable for all or part of the implant device 100 to be flexible. Flexibility allows dynamic integration and movement of the device 100 with dermis 230 and subcutaneous tissue 240. Human tissue is flexible and dynamic. It may be advantageous for the implant device 100 to be flexible and dynamic to move synchronously with tissue, thereby minimising shear forces at the interface between the epidermis 220 and the crowning element 120.

Ideally, the pore size in the tissue integration layer 110 is sufficiently large to preclude or minimise the likelihood of fibroblasts dying from hypoxia and lack of nutrients. Cell death is known to result in the pores filling with cell debris that in turn can lead to infection and failure of the device. A pore diameter of between 20 μm and 500 μm is acceptable. Ideally, however, a pore size of no smaller than 40 μm diameter is desirable. Additionally, there should be a negligible number of dead spaces, the pores should be highly interconnected, and there should be few acute angles in the pores. Acute angles, where the pore narrows down to less than 40 μm diameter, may predispose to cell death. Pore size, shape, and interconnectivity in the tissue integration layer 110 are optimised to permit tissue ingress particularly during application of negative pressure and also after the negative pressure has been removed. Effective integration of tissue into the tissue integration layer 110 anchors and protects the overlying epidermis 220 from avulsion forces. Advantageously, the application of negative pressure minimises or removes avulsion forces, which protects the epidermis 220 and thereby stabilises the device 100.

The tissue integration layer 110 and crowning element 120 may be formed of a single unitary piece of biocompatible material. Alternatively, the crowning element 120 may be formed separately from the tissue integration layer 110 and bonded, welded, brazed, fused or otherwise joined to form a single interface device 100 before or after implantation in the subject. In some embodiments, the device 100 or parts of it are manufactured using 3D printing or computer controlled material deposition. Depending on its size and/or application, the tissue integration layer 110 may comprise a number of repeating volumes of macroporous scaffold material although in some embodiments it may be desirable for a computer controlled 3D printer or material depositing apparatus to manufacture a randomised or substantially randomised structure. The shape of the scaffold of the tissue integration layer 110 can be highly variable. In some embodiments it is desirable that the shape of the tissue integration layer 110 represents the subject's "usual" anatomy at the site of implantation. For example, the site of implantation may include the subject's jaw or nose in circumstances where the natural anatomical structure has been removed due to illness or was never formed, and the tissue integration layer is shaped to provide such structure.

The crowning element 120, once implanted, provides a site for attachment of devices or insertion of devices and instruments to deeper tissues or organs.

Suitable materials for the interface device may include polymers and co-polymers, metals, non-metals and polymer-metal composites or a combination of these materials. One such combination with demonstrated suitability is the mixed macrodiol polyurethane co-polymer Elast-Eon™, as a toric shaped crowning element, melt-bonded to an underlying tantalum macroporous scaffold.

The crowning element 120 is ideally sized and shaped to optimise epidermal attachment to its surface. The shape may be e.g. toroid, discoid, polygonal or any other irregular or regular closed shape. The shape of the crowning element 120 may be determined according to the intended function of the interface device 100. For instance, an interface device 100 intended to couple with a single existing accessory device such as a catheter, drainage tube or perfusion line a particular through channel profile may be desirable. Generally, the channel 122 extends at least through a central portion of the crowning element 120 and as such, a toroid or discoid shape would be appropriate.

In other applications, e.g. where several access points are required (as may be required to anchor a prosthetic or robotic device to a limb), the shape of the crowning element 120 may be modified, enlarged or contoured to suit the accessory device and the body part to which it is being coupled. In some applications, the perimeter of the crowning element 120 may be regular, somewhat regular, or irregular. Alternatively/additionally, in some applications, there may be two or more crowning elements 120 on the tissue integration layer 110 providing two or more locations at which the interface device 100 extends through the epidermis 220 facilitating access to deeper tissues from outside the subject's body. Examples are provided in FIGS. 6 and 7.

Where no channel 122 is required, (e.g. for attachment of a prosthetic) negative pressure can be applied around the crowning element 120 to enhance tissue ingress into the macroporous structure of the tissue integration layer 110. In some embodiments, the crowning element 120 may have pores, micro-channels perforations or fenestrations to enhance distribution of the negative pressure through and between the crowning element and to the tissue integration layer 110 during implantation, thereby enhancing or encouraging tissue ingress into the pores of the tissue integration layer 110.

During implantation, tissue integration between the device 100, dermis 230, and subcutaneous tissue 240 begins around the outer surfaces of the tissue integration layer 110 and works toward the centre region of the crowning element 120 including channel 122 (where present). Pores in the tissue integration layer 110 that are close to subcutaneous tissue 240 experience subcutaneous tissue integration to a greater extent than pores in the tissue integration layer that are closer to the epidermis 220 and to some extent the dermis. Once the tissue integration layer is integrated into the dermis 230 and subcutaneous tissue 240, close tissue apposition to the scaffold structure provides a foundation and anchor for overlying epidermis. Once the device is implanted, part of the crowning element 120 protrudes through the epidermis 220 so that it is accessible from outside the subject's body.

A particular advantage arising from the structure of the interface device 100 disclosed herein is that it permits the transmission of negative pressure to the underlying tissue so that tissue integration into the porous structure of the tissue integration layer 110 anchors the device, while concurrently allowing attachment of the epidermis 220 to the crowning element 120 or upper tissue integration layer. This advantage has not hitherto been seen in implant devices or devices intended to interface with skin.

In some embodiments, the crowning element 120 includes one or more zones that have been functionalised with chemical functional groups to optimise epidermal 220 attachment to the crowning element 120. In some embodiments, the functionalised zone is protein optimised e.g. with collagen. It is known that cellular attachment to protein-optimised surfaces is faster and more robust than is the case for non-optimised surfaces.

Surface optimisation may involve a range of techniques for bonding chemical or biologically active molecules to the surface of the crowning element 120 to modify the extent to which epidermal attachment occurs. In one embodiment, glow discharge plasmas are used to create functionalised zones on the surface of the crowning element 120. The functionalised surface can then bind biologically active molecules such as proteins. Although any generic form of functionalisation may be suitable, Acetaldehyde plasma polymerisation (Aapp) has been determined by the inventor to be suitable for achieving surface functionalisation of the crowning element 120 for epidermal attachment.

Figure 12:
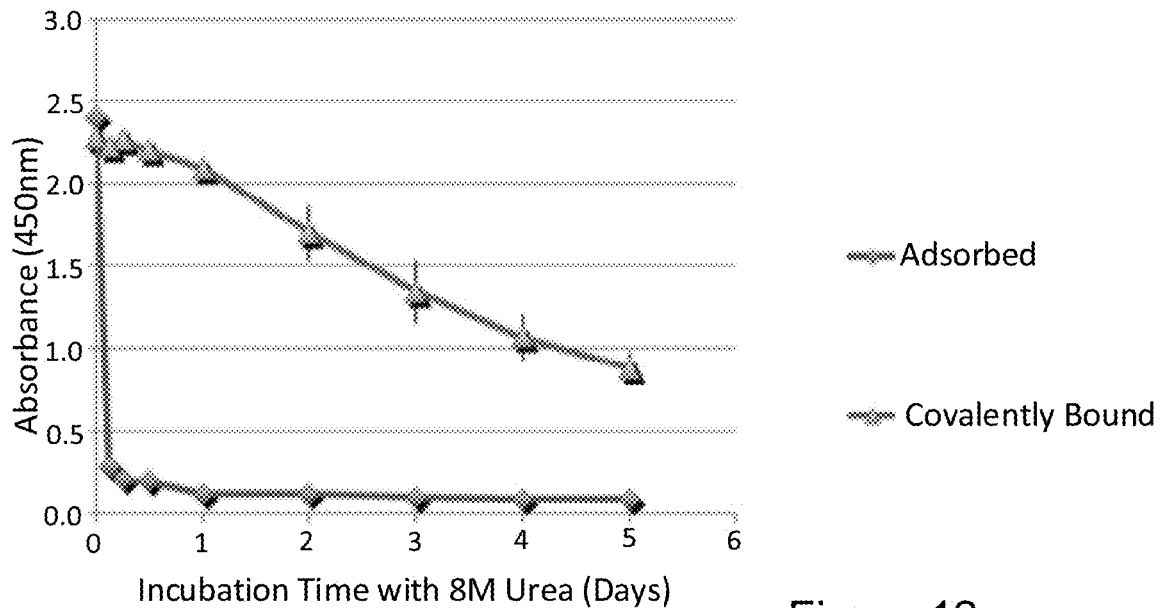
FIG. 12 shows results from the inventor's experiments demonstrating enhanced stability of collagen type 1 after covalent bonding to a biomaterial.
Figure 13:
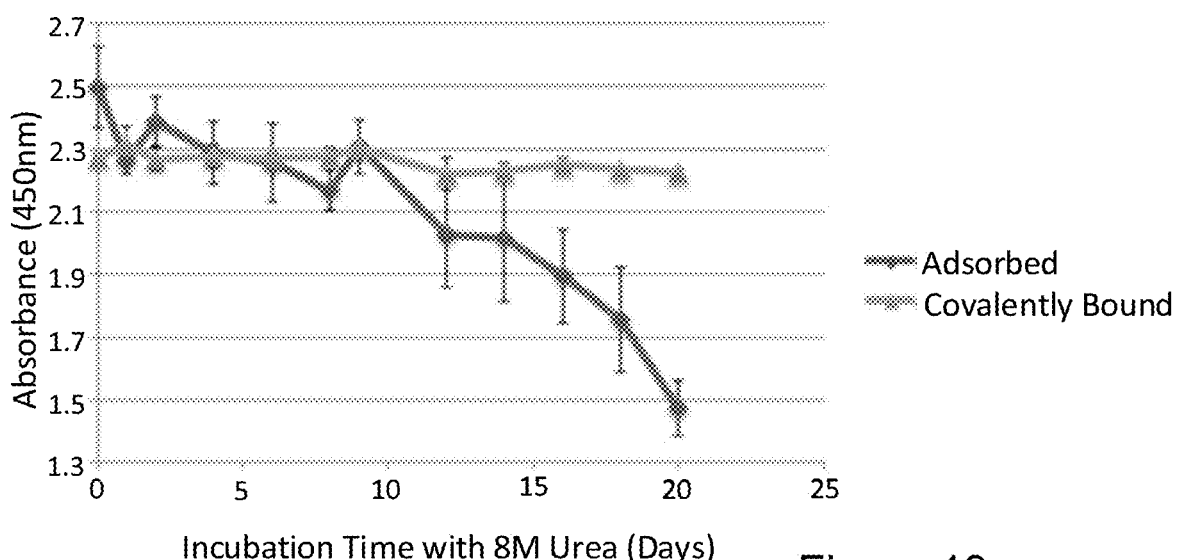
FIG. 13 shows results from the inventor's experiments demonstrating enhanced stability of collagen type 4 after covalent bonding to a biomaterial.

In published prior art, implants have been surfaced-optimised with collagen type 1. The inventor has undertaken research to assess the stability of collagen type 4 against collagen type 1 and discovered that, after incubation with 8M urea, collagen type 4 had much greater stability than collagen type 1. Results are shown in FIGS. 12 and 13 for adsorbed and covalently bound collagen (using Aapp) for collagen types 1 and 4 respectively. FIG. 12 shows that after less than one day, collagen type 1 was completely eluted from the specimens to which collagen type 1 was adsorbed, while 92% was retained on specimens that were Aapp functionalised (covalently bound). In contrast, the results in FIG. 13 show that adsorbed collagen type 4 was eluted to approximately 59% of its initial concentration after 20 days while surprisingly, covalently bound collagen type 4 showed no evidence of elution over the same period thus exhibiting starkly improved stability. Thus, the inventor has observed that covalent bonding significantly improved resistance to degradation and peeling-off of collagen type 4 from the tested biomaterial.

These results led the inventor to hypothesise that use of collagen type 4 in vivo will increase the longevity of implants. Accordingly, surface optimisation of the crowning element 120 with collagen type 4 is likely to enhance epidermal attachment to the crowning element. However, optimisation with collagen type 4 is not requisite for epidermal attachment to the crowning element 120. The surface of the tissue integration layer 110 and/or its junction with the crowning element 120 may also be optimised with collagen type 4 to stabilise the implant 100 and increase its longevity. For example, a coating of collagen type 4 may be applied to the surface of the tissue integration layer 110.

Figure 1B:
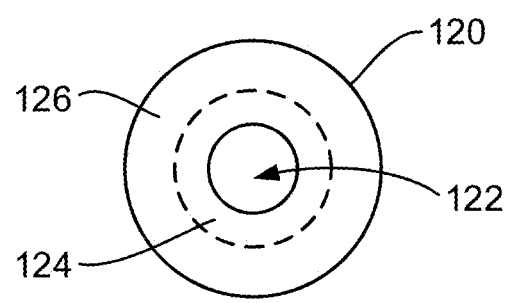
FIG. 1B is a top schematic illustration of a crowning element 120 with surface optimised zones.

The entire surface of the crowning element 120 may be optimised. Alternatively, as shown in FIG. 1B, surface optimisation may be confined to specific functional zones or applied in a pattern configured to achieve a functional outcome. For example, in areas of the crowning element 120 where it is desirable to enhance epidermal attachment, the functionalised zone 126 may be optimised with protein such as collagen type 4. Alternatively/additionally, in areas of the crowning element 120 where it is desirable for there to be no or minimal epidermal attachment, the functionalised zone 124 may be inert. Optionally, an area of the crowning element 120, such as zone 124 may be functionalised or treated with an agent to mitigate infection or other biological processes. In some applications epidermal attachment to the upper surface of the tissue integration layer 110 (but no deeper) is desirable to create a skin-biomaterial interface. In that case, the entire crowning element 120 may be changed to resist epidermal attachment so that epidermal marsupialisation alongside the crowning element may occur.

It is to be understood that the surface optimisation of the crowning element 120 is controllable and may therefore be restricted to discrete functionalised zones. Discrete functionalised zones may be achieved by close control of the plasma polymer coating process or other methods of surface functionalisation. Alternatively/additionally, areas not requiring surface treatment may be masked prior to subjecting the crowning element 120 to the optimisation process. Alternatively, the entire crowning element 120 may be optimised and the areas that do not require surface optimisation may be treated or covered to deactivate or obstruct active molecules outside the required functionalised zones.

Surface optimisation of the crowning element 120 may also occur through physical modification of the surface. For example, the entire surface or specific functionalised zones may be nanotextured, e.g. to either enhance or minimise epidermal attachment as may be desired (not shown). Additionally/alternatively, surface optimisation of the crowning element 120 may involve a combination of physical and chemical modification techniques. Ideally, surface optimisation is provided on a desired area (functionalised zone) of the crowning element. Such an area may include part or all of the junction between the crowning element 120 and scaffold of the tissue integration layer 110. Where minimal or no epidermal attachment is desired, the crowning element 120 may include an inert functionalised zone 124 that promotes epidermal marsupialisation. Alternatively, where epidermal attachment is desired, the crowning element 120 may include a functionalised zone 126 which acts to guide and promote epidermal attachment.

Figure 2:
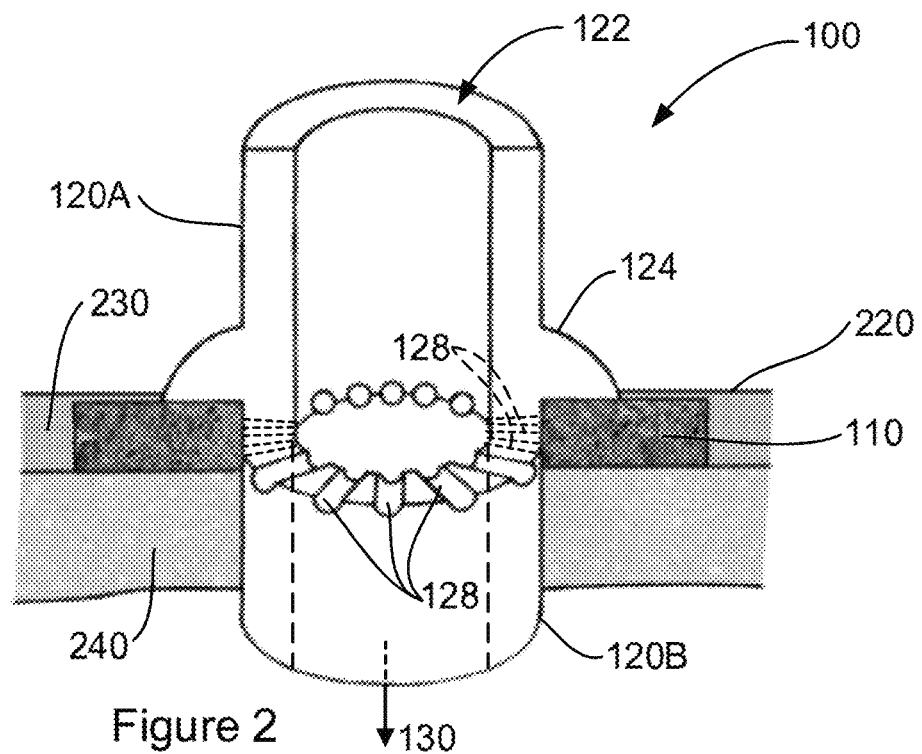
FIG. 2 is a schematic illustration of an interface device according to another embodiment of the invention, also shown in cross section.

In some embodiments, the crowning element 120 is shaped for coupling with or insertion of an accessory device or to provide a particular function such as drainage or fixation. Such an embodiment is illustrated in FIG. 2. Here, the crowning element 120 is shaped as a tube having an outer body portion 120A and an inner body portion 120B. A channel 122 formed through the crowning element 120 is in functional communication with pores of the tissue integration layer 110 via channels or pores 128 to facilitate tissue integration during implantation. Additionally, the inner portion 120B of the crowning element continues the hollow channel from outer body portion 120A forming a "through channel" 130 which permits transcutaneous access to deeper tissues.

Figure 3:
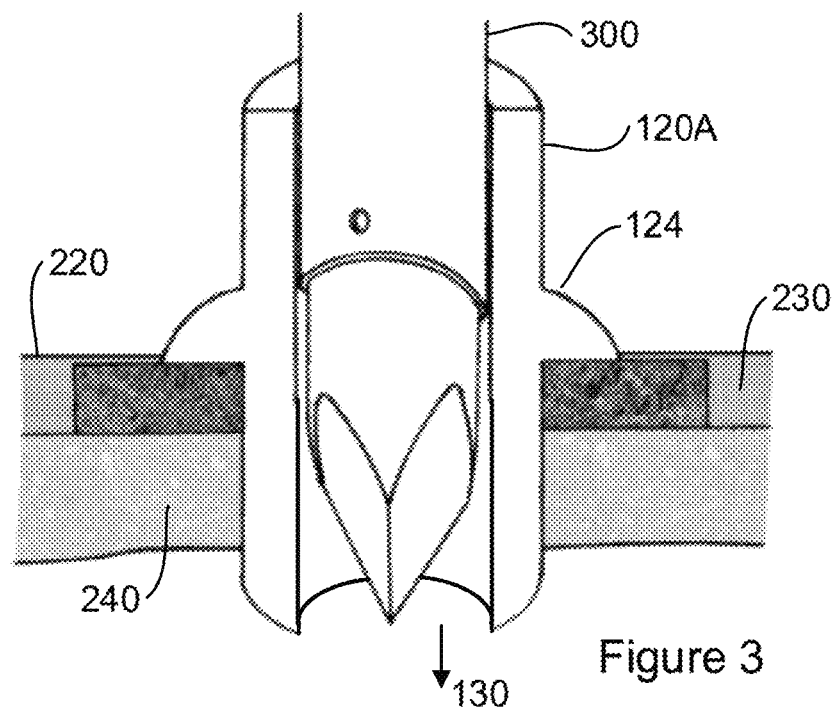
FIG. 3 is a schematic illustration of the interface device of FIG. 2 coupled with an accessory device in the form of a trocar.

FIG. 3 shows an accessory device 300, in the form of a trocar, inserted into deeper tissues via the through channel 130. Transcutaneous access via a trocar may be useful for introduction of catheters, tubes, miniaturised cameras and a variety of other instruments used to treat, inspect or manipulate deeper tissues.

A range of implantation devices may incorporate the interfacing technology described herein, such as e.g. bone anchored rods, bone screws, tubes and the like. In such arrangements, the functional rod, screw, tube or the like is incorporated into or replaces the inner body portion of the crowning element 120 which extends into the deeper tissue. These devices can use a similar method of implantation as for the interface device 100 shown in FIG. 1A.

Figure 4:
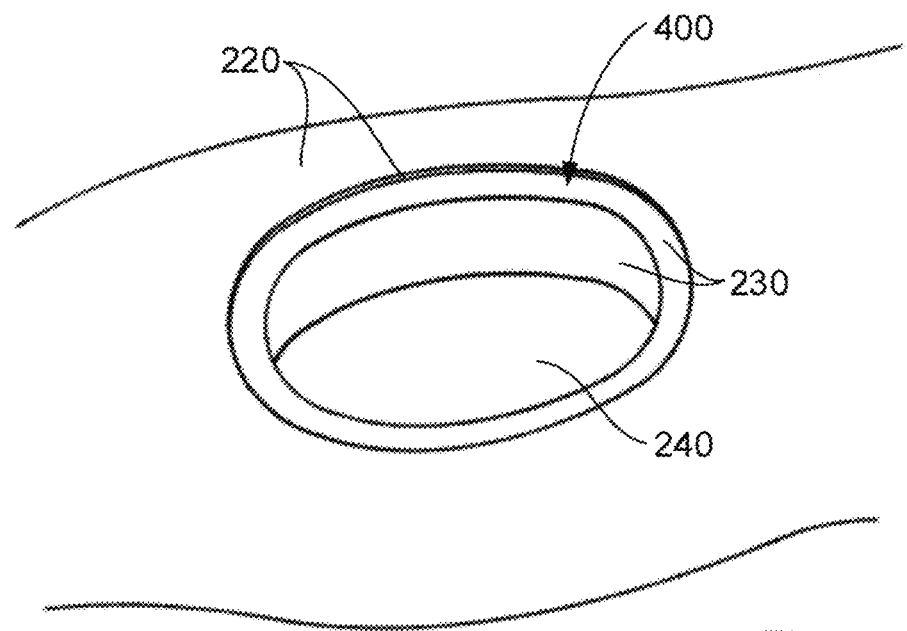
FIG. 4 is a schematic illustration showing an implant site prepared for implantation of a device according to an embodiment of the invention.

FIG. 4 shows a tissue implant site 400 which has been prepared for implantation of an interface device 100 according to an embodiment of the invention. An area of skin at the implant site 400 is de-epithelialized and a section of the dermis 230 and epidermis 220 is removed revealing subcutaneous tissue 240. In some embodiments, some subcutaneous tissue 240 may also be removed although this need not be the case to achieve effective tissue integration when the device 100 is implanted. Removal of a section of skin as shown creates a space at the implant site 400 that is sufficient to accommodate the tissue integration layer 110 of the interface device 100. It is to be understood that while FIG. 4 shows removal of a substantially circular section of dermis 230, the removed tissue section and hence the space created for the interface 100 may take any suitable shape. For example, the tissue integration layer may be square, round, oblong or have a three dimensional shape achieved by contoured excision of the dermis.

In some embodiments, it may be desirable to remove a larger area of the dermis 230 than the epidermis 220. This accommodates an interface device 100 as shown in FIGS. 1A to 3 with a crowning element 120 having a smaller diameter than the tissue integration layer 110 to which it is attached. In other embodiments involving smaller implant devices 100, preparing the tissue implant site 400 may involve forming a simple incision and inserting the device like a button into a button hole. In other cases still, larger area of skin is de-epithelialized and a smaller area of the dermis 230 below (and optionally subcutaneous tissue 240) is excised. The larger area of tissue is removed from the dermis 230 to accommodate the larger tissue integration layer 110 of the device 100. Tissue elasticity permits insertion of the interface device 100 when the size of the tissue integration layer 110 exceeds the size of the opening in the epidermis 220 and/or dermis 230. However, for simplicity, it may be desirable to remove a section of tissue having a somewhat regular shape.

Figure 5:
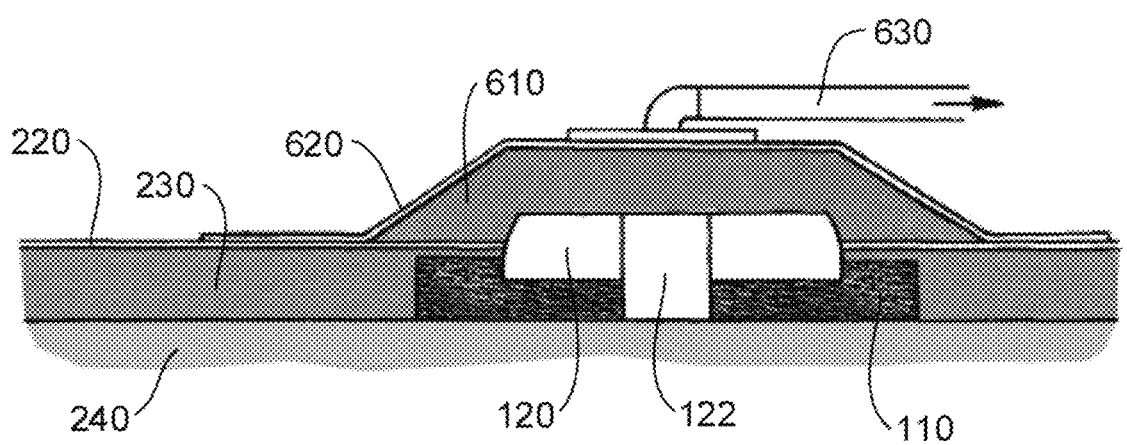
FIG. 5 is a schematic illustration showing the prepared implant site from FIG. 4, with the device implanted as in FIG. 1A and covered by a dressing with negative pressure applied according to an embodiment of the invention.

FIG. 5 shows the interface device 100 in cross section placed in a prepared implant site 400. A foam layer 610 is applied over the implant device 100. Plastic sheeting 620 is applied over the foam layer 610 (although the foam layer may, in some cases be substituted with gauze or other dressing material or omitted altogether). The plastic sheeting 620 forms a seal over the implant site 400 and a negative pressure is applied, through the dressing 620, via a tube 630. Application of a negative pressure increases vascularisation, improves tissue healing and granulation, and removes exudate and chemical mediators of inflammation, thereby enhancing tissue ingress into the pores of tissue integration layer 110.

The negative pressure may be generated by any suitable source such as a vacuum pump or the like. Ideally, the negative pressure source is configurable to apply a pressure between negative 25 mmHg and negative 500 mmHg over a pre-definable duration. Typically, the pressure applied during implantation is in the range of negative 125 mmHg +/−100 mmHg although pressures as low as negative 500 mmHg may be desirable in some applications.

Negative pressure may be applied continuously, intermittently or cyclically over a duration sufficient to achieve tissue integration into the pores of tissue integration layer 110. In most embodiments the duration is in the range of 1 to 28 days. Typically, a shorter duration of 1 to 15 or even 1 to 10 days is sufficient and in many applications, a duration of 6 to 7 days is sufficient to achieve adequate tissue integration although a duration as short as 2 to 6 days or even 2 to 3 days may be sufficient. In some cases, application of negative pressure for one day or for a few (e.g. 3 to 6) hours is sufficient. In most applications, cyclic application of negative pressures achieves tissue integration more effectively. For example, the desired negative pressure may be applied for a period of ten minutes followed by a period of no (or reduced magnitude) negative pressure for a period of two minutes, with the cycle repeated for the duration of tissue integration. Once tissue integration is complete, the negative pressure is disconnected, the dressing 620 and foam layer 610 are removed together with the tubing 630 and the interface device 100 remains in vivo.

Owing to the unique structure of the interface device 100, during the period of tissue ingress into the tissue integration layer 110, epidermal cells concurrently migrate over the tissue integration layer and adhere to the crowning element 120 (or upper aspects of the tissue integration layer if the crowning element is altered to resist epidermal attachment) such that, upon removal of the plastic sheeting 620, a portion of crowning element 120 (or the entire crowning element) protrudes through the epidermis 220. Upon removal of the plastic sheeting 620, foam 610 and tubing 630, the interface device 100 is anchored within dermal and subcutaneous tissue.

In some embodiments, it may be desirable to remove part of the tissue integration layer 110 in order to extend the crowning element channel 122 and provide a through channel 130 across the device for accessing deeper tissues, e.g. as shown in the embodiments shown in FIGS. 2 and 3. Removal of a "core" of the tissue integration layer 110 may be achieved using a drill, reamer or by puncturing the tissue integration layer using a sharp tipped device such as a trocar, needle or the like. In some embodiments, it may be desirable to remove the excised section of tissue integration layer 110 from the body. In other embodiments, the tissue integration layer 110 is partly or completely biodegradable.

In some embodiments, a channel formed through the implanted device 100 may require occlusion to close the interface access to deeper tissues. In such applications, a permanent or removable/reusable cap may be inserted through or applied over the channel 122 as required.

The size of the interface device 100 may be determined according to the clinical application for which the interface device is required. A diameter as small as 0.5 or 1 cm is sufficient to support long-term integration of the device in the dermis 230. Similarly, the shape of the device may be determined according to the clinical application. Embodiments illustrated herein show a circular and substantially toric device with a channel 122 extending though the thickness of the crowning element 120. As described above, in some embodiments, the channel 122 may be extended, through the tissue integration layer 110 to provide a through channel 130 for accessing deeper tissues of the subject. It is to be understood, however, that the tissue integration layer 110 may have any size or shape. In some embodiments, the tissue integration layer 110 has a generic shape and is configured or trimmed to the required size just prior to implantation.

Figure 9:
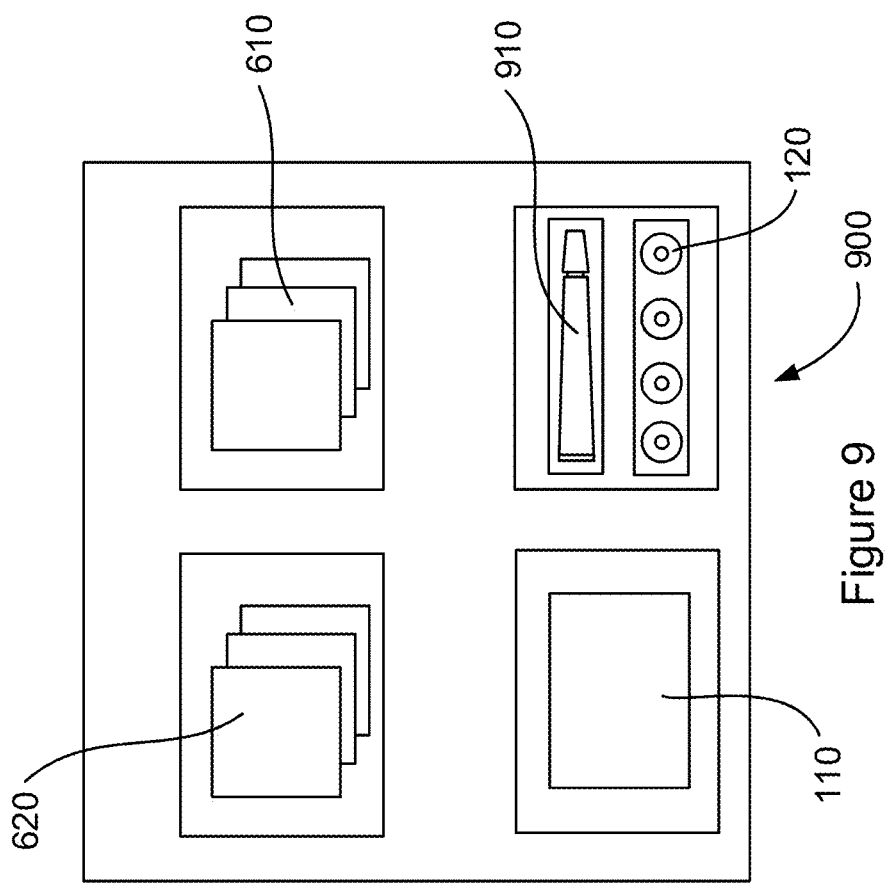
FIG. 9 is a schematic illustration of a kit according to an embodiment of the invention.

In some embodiments, the interface device 100 is supplied as a unitary piece with the tissue integration layer 110 and the crowning element 120 pre-attached. In other embodiments, the implant device 100 is provided in a kit 900 (FIG. 9) containing a generic macroporous tissue integration layer 110 and one or more crowning elements 120. An adhesive or bonding agent 910, anchors or other fixation devices for attaching one or more crowning elements 120 to the tissue integration layer 110 may also be provided in the kit. Ideally, one or more foam layers 610 and adhesive plastic sheets 620 are also provided in the kit together with tubing 630 (not shown) for connecting the interface device, once covered by the dressing with a negative pressure pump (not shown).

When the interface device 100 is provided in kit form, a clinician can trim the generic macroporous tissue integration layer 110 to the desired size and shape, and apply one or more crowning elements 120 to the tissue integration layer 110 at locations that are determined for a specific clinical application. The interface device 100 may be assembled by attaching one or more crowning elements 120 to the tissue integration layer 110 before it is implanted, or the tissue integration layer may be placed first, and a crowning element 120 attached to the tissue integration layer at the implant site.

Figure 6:
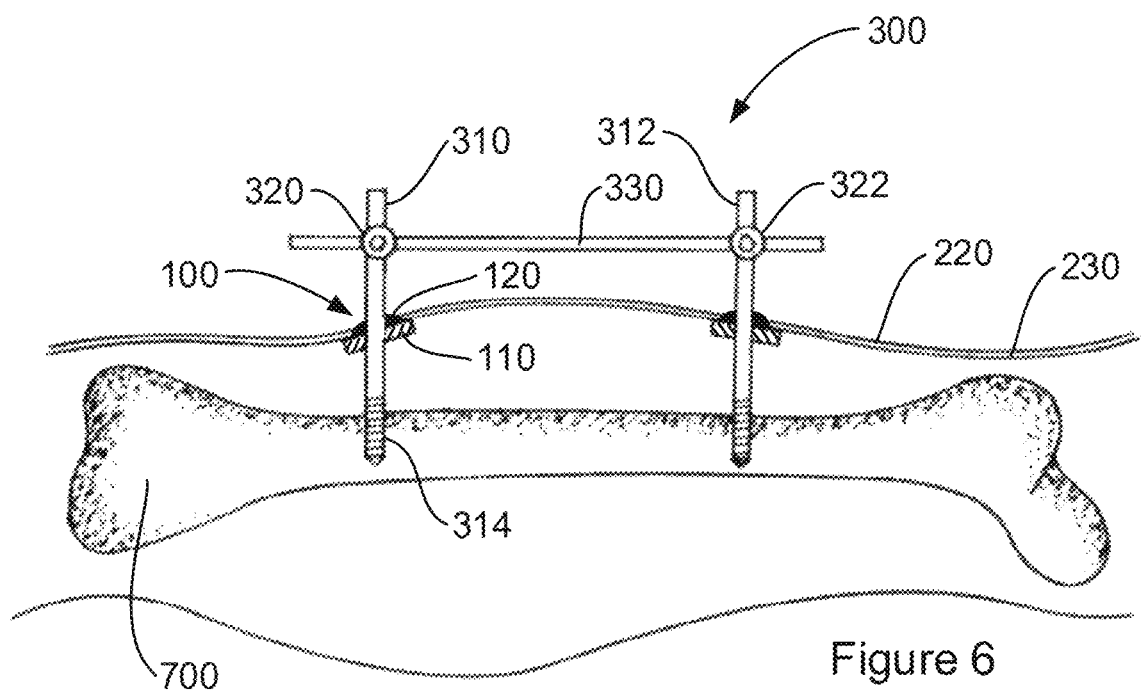
FIG. 6 is a schematic illustration of the interface device used with an accessory device according to another embodiment of the invention and used with a bone fixation screw.

FIG. 6 shows interface devices 100 used with an accessory device 300 in the form of bone screws 310, 312, plate 330 and external fixation screws 320, 322. In this embodiment, an interface device 100 is used at the point of transcutaneous entry for each of the bone screws 310, 312 into the subject's body. In one embodiment, the interface device 100 is implanted in accordance with a method described in relation to FIGS. 4 and 5 prior to inserting the bone screws 310, 312. Once there is effective tissue integration, a bone screw 310 is inserted through channel 122 in the crowning element 120 in one of the implanted devices 100 and the threaded shaft 314 is screwed through the tissue integration layer 110 so that the screw penetrates the entire depth of the interface device 100 and accesses the deeper tissues. The bone screw 310 is then advanced toward and into the bone 700, where the threaded shaft 314 engages the bone to achieve fixation. The process is repeated with second bone screw 312. An external fixation plate 330 is then attached to stabilise the bone screws 312, 314 using external fixation screws 320, 322.

In another approach, the bone screws 310, 312 may be assembled with an interface device 100 ex-vivo. That is, prior to implantation of the device, a bone screw 310 is inserted into the channel 122 in the crowning element 120 and the threaded shaft 314 is screwed through the tissue integration layer 110 so that the bone screw 310 rotates freely inside a through channel 130 that it forms through the full thickness of the interface device 100. In a single procedure, a layer of the dermis is removed to create an implant site 400 as described above, and the interface device is implanted using the method discussed above with the bone screw 310 extending therethrough. The bone screw 310 is then advanced into the deeper tissues, toward and into the bone 700 where the threaded shaft 314 is screwed into the bone. Foam layer 610 and plastic sheeting 620 are then applied over and/or around the external portion of the bone screw 310 forming a seal, and negative pressure is applied to encourage ingress of tissue into the pores of the tissue integration layer 110 through which the bone screw 310 extends.

Figure 7:
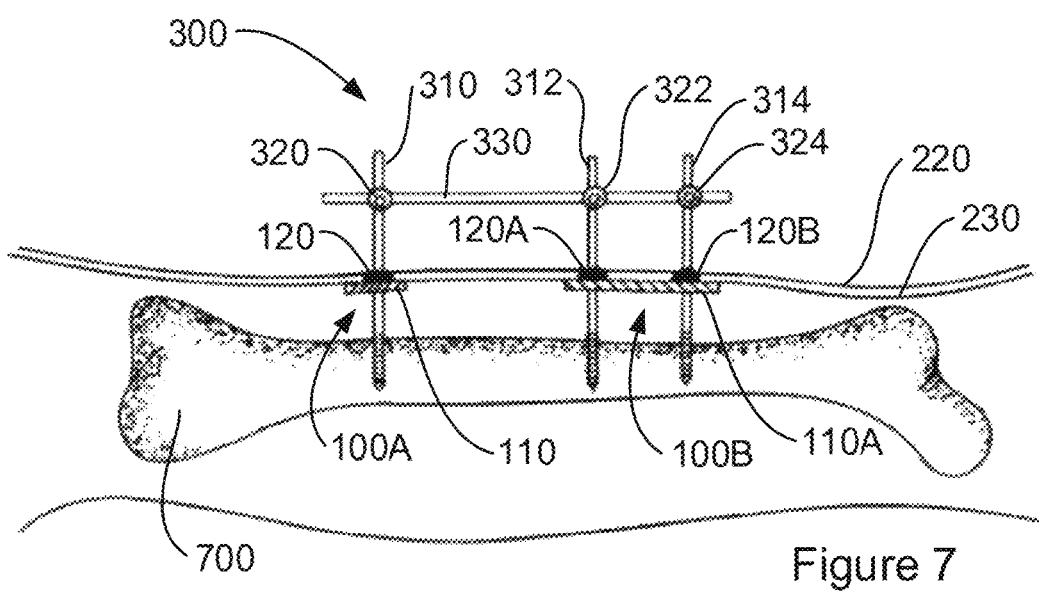
FIG. 7 is a schematic illustration of the interface device that is a modification of the device illustrated in FIG. 5 and used with a similar accessory device.

FIG. 7 shows a similar embodiment to FIG. 6, with a bone screw 310 inserted through a first interface device 100A and into bone 700 with an external portion of the bone screw 310 attached to an external fixation plate 330 by external fixation screw 320. Additionally, a second interface device 100B is provided, through which two bone screws 312, 214 have been inserted. Bone screws 312, 214 are also attached to the external fixation plate 330 by external fixation screws 322, 324. In this embodiment, the interface device 100B has two crowning elements 120A, 120B which extend through the epidermis 220 at different locations, though both are commonly anchored in the dermis 230 by a single tissue integration layer 110A. Advantageously, the common tissue integration layer 110A provides an additional stabilising anchor for bone screws 312, 314. Either implantation method described with respect to the embodiment shown in FIG. 6 may be used for implantation of one or both of the interface devices 100, 100A shown in FIG. 7.

In some clinical applications an implanted interface device may be required for permanent implantation e.g. in the case of prosthetics. In other applications, the interface device may be required to remain in vivo for an extended period of weeks, months or even years and may be explanted from the patient when no longer required. In some embodiments, the tissue integration layer is biodegradable in the biological environment leaving only the crowning element 120 in the epidermis 220 and dermal tissue 230 for removal. For example, in a patient receiving chemotherapy, it may be desirable for the tissue integration layer to biodegrade after the completion of chemotherapy, leading to spontaneous extrusion of the crowning element. Alternatively, depending on the size of the interface device, explantation may be a simple procedure performed with local anaesthetic and requiring few or no stitches. In other cases where the interface device is larger, a skin graft or flap may be required.

In some cases, such as in FIGS. 6 and 7 after effective bone fixation is achieved, the accessory device, in this case the bone screws 310, 312, 314, may be removed. The interface devices 100, 100A can remain in vivo, with a cap or plug closing the channel 122. Advantageously, if the bone fixation subsequently fails, the cap can be removed and the interface device 100, 100A re-used for infection free access to the bone. Alternatively, the implant device can be explanted or removed as described above.

Figure 10:
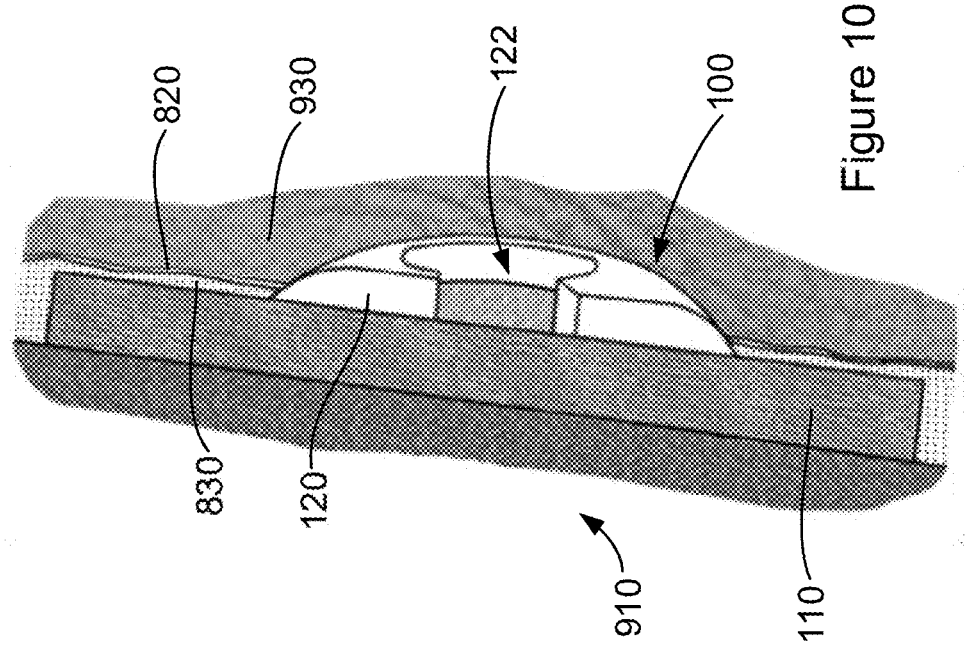
FIG. 10 is a schematic illustration showing implantation of an interface device in the aortic wall, according to an embodiment of the invention.

The principles illustrated in the bone fixation examples of FIGS. 6 and 7 can be applied in a range of clinical applications requiring safe, infection free, long term transdermal attachment of a device or access to deeper tissues, body cavities or blood vessels. It is to be understood, however, that embodiments of the inventive interface device may be used entirely internally in any situation involving epithelium or endothelium and deeper tissue, e.g. to provide an interface across a blood vessel, the gut, bladder, pleural cavity or the like. An example is shown in FIG. 10, where an interface device 100 is implanted in the wall of the aorta 930. Here, tissues of the aortic wall 830 ingress into the tissue integration layer 110 during implantation, while the crowning element 120 acts as an attachment point for luminal endothelium 820, all (ideally) with the assistance of negative pressure. This device can be used to provide trans-aortic access to the abdomen 910 and surrounding tissues.

In other embodiments, the interface device 100 may provide a tissue integration layer 110 adapted for integration of a number of different tissue types. Thus, in addition to the tissue structures involved with skin integration such as adipocytes, fibroblasts, and collagen, ingress of other cell types such as myoblasts and osteoblasts may be seen with integration into muscle and bone. Alternatively/additionally, the crowning element 120 may extend through the tissue integration layer 110 as in FIGS. 2 and 3, to perform a particular function in the deeper tissue. By way of example, an inner body portion 120B of the crowning element 120 may terminate in or provide a thread, hook or anchor for engaging bone, cartilage or other tissue.

Figure 8A:
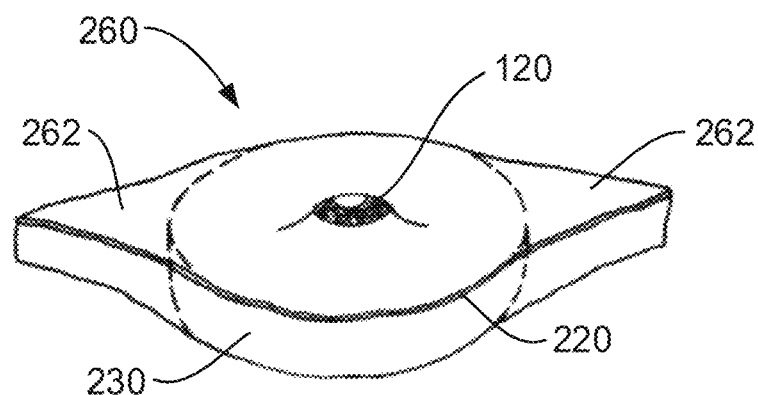
FIG. 8A is a schematic illustration of an implanted device excised from the implant site with integrated tissue and ready for grafting to another site.
Figure 8B:
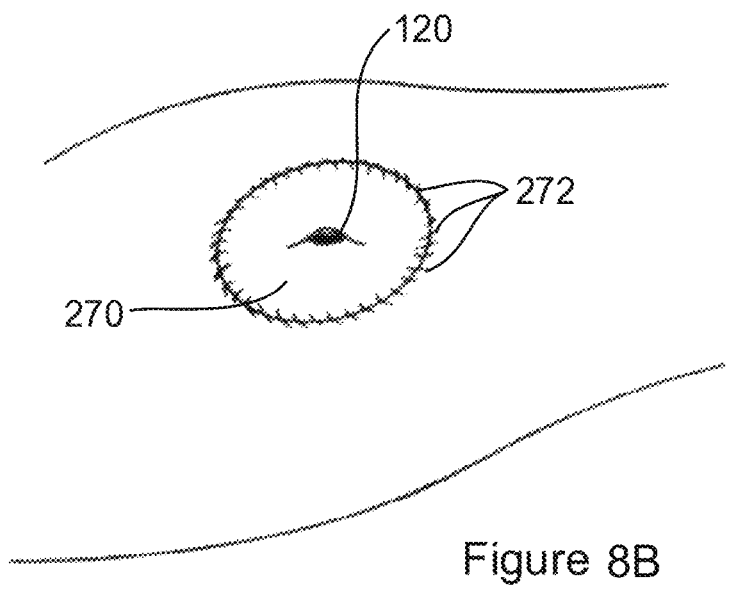
FIG. 8B is a schematic illustration showing the excised device from FIG. 8A grafted to a recipient site.

FIG. 8A is a schematic illustration of a section of excised tissue 260 into which an interface device 100 has been implanted according to embodiments of the invention. There is full tissue integration at the dermis 230 and epidermal attachment to the crowning element 120 such that only a small portion extends through the epidermis 220 to facilitate external access. Typically, the section of excised tissue 260 is elliptical and is trimmed to remove triangular end portions 262 prior to grafting. The excised tissue 260 contains a safe margin of tissue and can be grafted elsewhere on the subject. FIG. 8B shows the trimmed excised tissue 270 containing the implanted interface device 100 grafted into a site that has been prepared in the same way as the implant site 400 in FIG. 4, with the section of dermis 230 that has been removed from the recipient site prepared to receive the shape of the trimmed excised tissue 270.

Advantageously, tissue integration has already occurred in the interface device 100 in explanted tissue 260. Accordingly, grafting requires no negative pressure and enables the interface device to be utilised in regions of the body (including internally) where application of a plastic sheeting 620 and negative pressure is challenging or impractical. Sutures 272 or a sterile dressing (not shown) over the recipient site 270 may be all that is required for tissue healing, thereby providing safe, infection free, long term attachment of an interface device for access to deeper tissues, body cavities or blood vessels.

Once implanted, the interface device 100 provides a mechanism for transcutaneous access to deeper tissues including underlying blood vessels and body cavities. This access may be directly through a channel 122 in the interface device 100 or via a tube or other accessory device 300 inserted through the channel 122 or functionality built into the tissue integration layer 110 or an inner body portion of the crowning element 120. Alternatively/additionally, the implanted interface device 100 provides an attachment site for other biomaterials and devices. In other embodiments still, the implanted device 100 provides for extended vascular access, peritoneal cavity access, pleural cavity access, bladder access, organ access, or airway access. Such access may permit delivery of medications, fluids, nutrition, gas (e.g. air via a tracheostomy tube) or drainage of fluid (e.g. urine from the bladder or pleural fluid from the pleural cavity).

As described herein, the accessory device 300 may include a trocar, tube, drain, prosthetic, electronic device, robotic device, catheter, ostomy device, drug delivery device, fixation device, and tissue building scaffold to name a few. In such devices 300, negative pressure can be delivered to deeper tissues via the fenestrations in the crowning element 120 or via the lumen of the trocar, tube, drain, catheter or ostomy device. In some embodiments, implanted device 100 may also allow later introduction, integration and attachment of a trocar, tube, drain, catheter or ostomy device.

Recent improvements in the area of peritoneal dialysis include new dialysis solutions, better delivery tubes, and cyclers for automated peritoneal dialysis. Notwithstanding these advances displacement, cuff extrusion, leakage, and infection remain problematic. Infection of the peritoneal dialysis catheter at the skin interface is a particular concern. Catheter-related infections can lead to cellulitis, necrotising fasciitis, and peritonitis. Advantageously, long-term and safe access to the peritoneal cavity can also be achieved using the inventive interface device.

Figure 11:
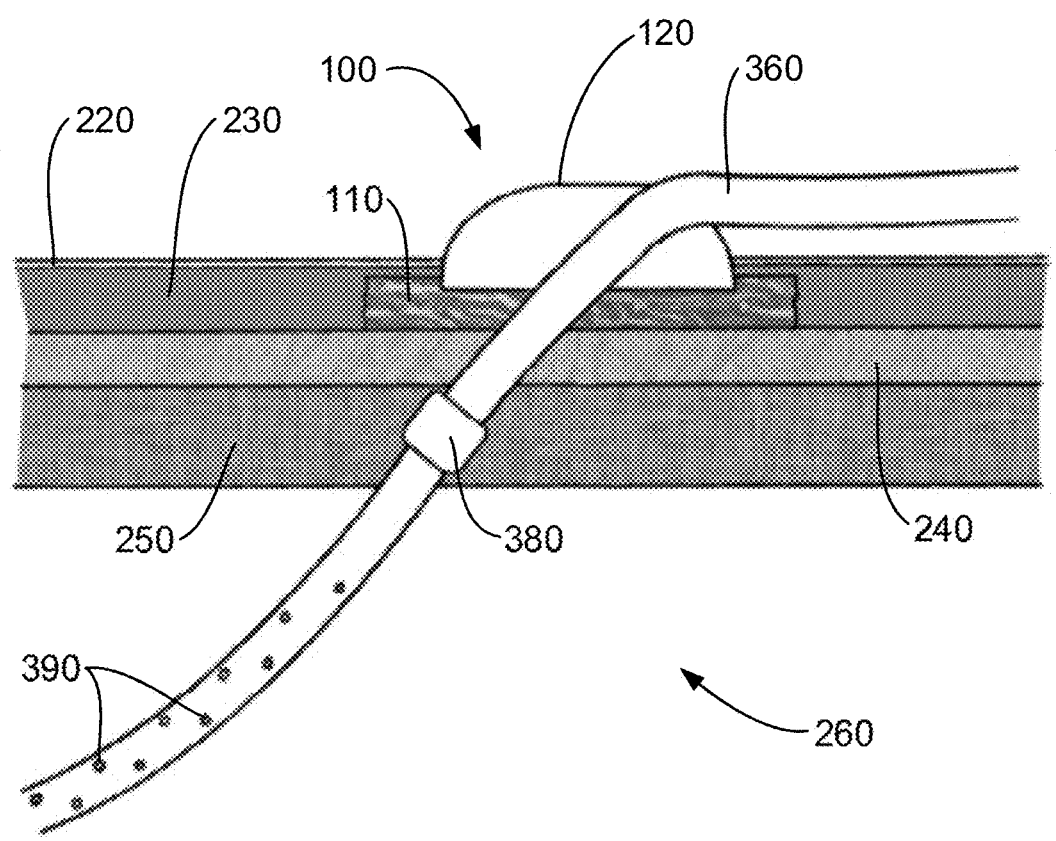
FIG. 11 is a schematic illustration showing use of embodiments of the invention for interfacing with a subject's abdominal wall to perform peritoneal dialysis.

FIG. 11 is a schematic illustration showing an embodiment of the invention for accessing the peritoneal cavity 260 to perform dialysis. Here, interface device 100 has been implanted for transcutaneous access as described previously. In use, a polymer dialysis tube 360 is passed through the implant device 100, crosses the abdominal wall 250 and enters the peritoneal cavity 260 where dialysate is delivered through holes 390 in the dialysis tube. A deep cuff 380 (known in the art) placed in the abdominal wall 250 stabilises the dialysis tube 360 internally. The embodiment illustrated in FIG. 11 shows the through channel in crowning element 120 and tissue integration layer 110 oriented at an angle that permits the dialysis tube 360 to rest comfortably along the subject's abdomen.

The implanted device 100 can enable long-term access to the gut, body organs, and the central nervous system. For example, embodiments of the inventive interface device are suitable for achieving drainage of the urinary tract (kidneys, ureters, or bladder). In other embodiments still, the implanted device 100 may itself, be extended into or form part of a prosthetic device.

In some cases, the inventive device may be used in the reconstruction of surgical, traumatic or congenital tissue defects. For example, following resection of a cancer involving the mandible, a tissue integration layer 110 could be shaped (using 3D printing, moulds, trimming or other techniques) to bridge the bone gap and/or subcutaneous tissue and dermis gap. A crowning element 120 attached to the tissue integration layer 110 could be used to bridge the skin gap. Tissue integration would be assisted by application of a negative pressure as described elsewhere herein.

In yet other cases, the inventive device may be used to form a robotic prosthetic limb. The crowning element 120 forms the "prosthetic" or acts as an attachment point for the prosthetic device, while the tissue integration layer and crowning element work together to form a long term, infection free interface with skin.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof It is to be understood that various modifications, additions and/or alterations may be made to the parts previously described without departing from the ambit of the present invention as defined in the claims appended hereto.

It is to be understood that the following claims are provided by way of example only, and are not intended to limit the scope of what may be claimed in future. Features may be added to or omitted from the claims at a later date so as to further define or re-define the invention or inventions.

What is claimed is:

1. An interface device for implantation in a subject, the device including:
   a. a tissue integration layer having a porous structure forming a scaffold into which tissue integrates to anchor the device when implanted;
   b. a crowning element attached to an upper surface of the tissue integration layer and configured such that once implanted, there is epidermal attachment to part of the crowning element, and part of the crowning element extends through the epidermis and is accessible from outside the subject's body;
   c. a seal capable of applying negative pressure overlaying the part of the crowning element accessible from outside the subject's body; and
   d. a source of negative pressure;
   wherein the porous structure of the tissue integration layer is interconnected for tissue ingress during implantation; and wherein the tissue integration layer is sized and shaped to provide a foundation that supports the crowning element such that when implanted, the tissue integration layer is entirely anchored beneath the epidermis.

2. The device according to claim 1, wherein the crowning element includes a functionalised zone that is optimised for epidermal attachment.

3. The device according to claim 1, wherein tissue integration into the porous structure of the tissue integration layer is enhanced by application of negative pressure to the device during implantation, wherein the tissue integration layer has one or more of: a compressive strength sufficient to resist compression during application of negative pressure.

4. The device according to claim 1, wherein the porous structure is macroporous and highly interconnected such that the tissue integration layer has no dead spaces, and contains pores having diameter of 20 µm to 500 µm, and preferably, at least 40 µm.

5. The device according to claim 1, wherein the device has at least one of the following properties:
   (a) the tissue integration layer and the crowning element are formed as a unitary piece;
   (b) the device is formed from one or more biocompatible materials selected from the group comprising: a polymer, a metal, a polymer-metal composite, a ceramic, and combinations including two or more of the foregoing;
   (c) one or more of the tissue integration layer, the crowning element and the device as a whole are at least partly flexible;
   (d) the crowning element includes a magnetic or electronic material;
   (e) at least part of the device is biodegradable in the subject's body;
   (f) a plurality of crowning elements configured to extend through the epidermis when implanted, providing a plurality of access points outside the subject's body;
   (g) the crowning element is sized and shaped to optimise epidermal attachment, wherein the shape is selected from a group comprising toroid, discoid, polygonal, irregular or regular closed shape; and
   (h) the crowning element is adapted to be coupled with or receive an accessory device, wherein the accessory device is selected from a group comprising a trocar, tube, drain, prosthetic, electronic device, robotic device, catheter, ostomy device, drug delivery device, a fixation device and tissue building scaffold.

6. The device according to claim 1, wherein the crowning element has one or more channels in functional communication with pores of the tissue integration layer, wherein part of the tissue integration layer is removable to extend a channel in the crowning element to form a through channel providing access to deeper tissues when implanted, and wherein the through channel provides for one or more of removal of fluid from the subject and an access point for insertion of an instrument or other accessory device.

7. The device according to claim 2, wherein the functionalised zone is protein optimised, and preferably, wherein the protein is collagen type 4.

8. The device according to claim 1, wherein the crowning element includes one or more functionalised zones that are optimised for either epidermal attachment or epidermal marsupialisation, and optionally, wherein the one or more functionalised zones are provided on the crowning element and may include a junction between the crowning element and the tissue integration layer.

9. A kit including:
   a. a piece of macroporous tissue integrating material providing a scaffold for receiving ingress of stabilising tissue and sized and shaped to provide a stabilising foundation;
   b. one or more crowning elements attachable to the stabilising foundation provided by the tissue integrating material;
   c. one or more seals capable of applying negative pressure overlaying the one or more crowning elements; and
   d. a source of negative pressure;
   wherein the one or more crowning elements are affixable to an upper surface of the stabilising foundation provided by the macroporous tissue integrating material to form an implantable interface device for use in a human or animal subject; and
   wherein the macroporous tissue integrating material is sized and shaped to provide a stabilising foundation that anchors the device such that when implanted, the macroporous tissue integrating material is entirely anchored beneath the epidermis.

10. The kit according to claim 9, wherein the one or more crowning elements include one or more functionalised zones that are optimised for epidermal attachment or epidermal marsupialisation.

11. A kit according to claim 9, further including one or more of an adhesive, a bonding agent and one or more anchors for affixing one or more crowning elements to the tissue integrating material, and including a dressing and tubing for connecting the interface device with the source of negative pressure.

12. The kit according to claim 9, wherein the piece of macroporous tissue integrating material comprises a highly interconnected structure having no dead spaces and containing pores having a diameter of 20 µm to 500 µm.

13. The device according to claim 1, wherein the seal capable of applying negative pressure is removable.

14. The device according to claim 1, including fenestrations in the crowning element to enhance transmission of negative pressure between the crowning element and the pores of the tissue integration layer.

* * * * *